(12) United States Patent
Kamisho et al.

(10) Patent No.: US 11,946,856 B2
(45) Date of Patent: Apr. 2, 2024

(54) METHOD FOR ESTIMATING STEEL RUPTURE STARTING POINT, DEVICE FOR ESTIMATING STEEL RUPTURE STARTING POINT, AND PROGRAM FOR ESTIMATING STEEL RUPTURE STARTING POINT

(71) Applicant: Nippon Telegraph and Telephone Corporation, Tokyo (JP)

(72) Inventors: Takuya Kamisho, Musashino (JP); Masamitsu Watanabe, Musashino (JP); Yosuke Takeuchi, Musashino (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 723 days.

(21) Appl. No.: 17/053,565

(22) PCT Filed: Apr. 24, 2019

(86) PCT No.: PCT/JP2019/017461
§ 371 (c)(1),
(2) Date: Nov. 6, 2020

(87) PCT Pub. No.: WO2019/216224
PCT Pub. Date: Nov. 14, 2019

(65) Prior Publication Data
US 2021/0231556 A1    Jul. 29, 2021

(30) Foreign Application Priority Data

May 7, 2018    (JP) .................................. 2018-089370

(51) Int. Cl.
*G01N 17/00*    (2006.01)
*G01N 33/2045*    (2019.01)

(52) U.S. Cl.
CPC ....... *G01N 17/006* (2013.01); *G01N 33/2045* (2019.01)

(58) Field of Classification Search
CPC .................... G01N 17/006; G01N 33/2045
See application file for complete search history.

(56) References Cited

U.S. PATENT DOCUMENTS

| | | | | |
|---|---|---|---|---|
| 6,699,335 | B2 * | 3/2004 | Murakami | F16C 33/62 148/320 |
| 7,035,746 | B2 * | 4/2006 | Wada | G01N 33/2045 702/81 |

(Continued)

FOREIGN PATENT DOCUMENTS

| | | | |
|---|---|---|---|
| CN | 1811000 A | * | 8/2006 |
| CN | 100410410 C | * | 8/2008 |

(Continued)

OTHER PUBLICATIONS

International Search Report dated Jul. 30, 2019, issued in PCT Application No. PCT/JP2019/017461, filed Apr. 24, 2019.

(Continued)

*Primary Examiner* — Octavia Davis Hollington
(74) *Attorney, Agent, or Firm* — Workman Nydegger

(57) ABSTRACT

To estimate a fracture starting point of steel due to hydrogen embrittlement with high accuracy. A steel fracture starting point estimation device includes a hydrogen concentration distribution calculation unit adapted to calculate a hydrogen concentration distribution in steel-to-be-estimated when the steel fractures due to hydrogen embrittlement; a local critical hydrogen content calculation unit adapted to calculate critical hydrogen content at which the steel-to-be-estimated fractures due to hydrogen embrittlement; and a fracture starting point estimation unit adapted to read the hydrogen concentration distribution out of a storage unit. To estimate, calculate, from the hydrogen concentration distribution, a (Continued)

location in the steel in which hydrogen concentration of the critical hydrogen content is distributed, and designate the location in the steel as the fracture starting point of the steel-to-be-estimated.

8 Claims, 3 Drawing Sheets

(56) References Cited

U.S. PATENT DOCUMENTS

| | | | | |
|---|---|---|---|---|
| 7,887,648 | B2* | 2/2011 | Kinugasa | C22C 38/50 |
| | | | | 148/333 |
| 9,151,706 | B2* | 10/2015 | Wada | G01N 17/00 |
| 2011/0005645 | A1* | 1/2011 | Murakami | C22C 38/04 |
| | | | | 148/579 |
| 2020/0188901 | A1* | 6/2020 | Kittel | G01N 17/04 |

FOREIGN PATENT DOCUMENTS

| | | | |
|---|---|---|---|
| CN | 101558174 B | * | 3/2013 |
| JP | 2004-340817 A | | 12/2004 |
| JP | 2007198895 A | * | 8/2007 |
| JP | 2009069007 A | * | 4/2009 |
| JP | 2010054494 A | * | 3/2010 |
| JP | 2017187441 A | * | 10/2017 |
| JP | 2016-45158 A | | 4/2019 |

OTHER PUBLICATIONS

Tetsuo Shiraga, *Hydrogen Embrittlement of Steel*, Materials and Environment, vol. 60, No. 6, 2011, pp. 236-240.

Shusaku Takagi et al., *Evaluation of Hydrogen Crack Susceptibility in High-Strength Steels*, Iron and Steel Telsu-to-Hagane, vol. 86, No. 10, 2000, pp. 689-696.

Toshinao Minakuchi et al., *Experimental Analysis of the Hydrogen Embrittlement of Cathodically Charged SNCM 439 Steel*, Journal of the Japan Society of Mechanical Engineers (Part A), vol. 56, No. 522, 1990, Paper No. 89-0374A, pp. 304-309.

Yukito Hagiwara et al., *Evaluation of Delayed Fracture Characteristics of High Strength Steel by CSRT Method*, Iron and Steel Tetsu-to-Hagane, Vo. 94, No. 6, 2008, pp. 27-33.

* cited by examiner

METHOD FOR ESTIMATING STEEL RUPTURE STARTING POINT, DEVICE FOR ESTIMATING STEEL RUPTURE STARTING POINT, AND PROGRAM FOR ESTIMATING STEEL RUPTURE STARTING POINT

TECHNICAL FIELD

The present invention relates to a technique for estimating a fracture starting point of high-strength steel due to hydrogen embrittlement.

BACKGROUND ART

High-strength steel suffers ductility loss and significant strength reduction due to hydrogen penetrating into the steel. This phenomenon is called hydrogen embrittlement (Non-Patent Literature 1).

Fracture of steel due to hydrogen embrittlement is thought to be caused by locally accumulated hydrogen and is said to occur when local hydrogen content in steel reaches or exceeds a threshold. For example, when a notched test piece with a groove formed in a surface thereof is used, hydrogen will accumulate on a notch root, producing a local stress concentration site, and the stress concentration site is considered to serve as a fracture starting point of steel (Non-Patent Literature 2).

Also, in examining a fracture starting point after fracture of steel due to hydrogen embrittlement, a method is used that involves observing a fracture surface under a microscope or the like and estimating the fracture starting point from a fracture form (Non-Patent Literature 3).

CITATION LIST

Non-Patent Literature

Non-Patent Literature 1: Shiraga, et al., "Hydrogen Embrittlement of Steel" Zairyo-to-Kankyo, 2011, p. 236-p. 240

Non-Patent Literature 2: Takagi, and five others, "Parameters for the Evaluation of Hydrogen Embrittlement of High Strength Steel" Tetsu-to-Hagane, 2000, Vol. 86, No. 10, p. 689-p. 696

Non-Patent Literature 3: Mizuguchi, and two others, "Brittle Fracture Condition for Delayed Fracture of High Strength Steel" Transactions of the Japan Society of Mechanical Engineers Series A, February 1990, Vol. 56, No. 522, p. 304-p. 309

Non-Patent Literature 4: Hagihara, and five others, "Evaluation of Delayed Fracture Characteristics of High Strength Steel based on CSRT Method" Tetsu-to-Hagane, 2008, Vol. 94, No. 6 pp. 215-221

SUMMARY OF THE INVENTION

Technical Problem

However, in actual environments, high-strength steel has various forms, and when a smooth test piece without a notch is used, there is no notch root where hydrogen can accumulate and a stress concentration site is unknown, making it difficult to estimate a fracture starting point. Even if a method for observing a fracture surface under a microscope is used, it is difficult to clearly identify a convergent point of a streaky wavefront regarded to be a fracture starting point, and the fracture starting point can be estimated only with coarse accuracy.

The present invention has been made in view of the above circumstances and has an object to estimate a fracture starting point of steel due to hydrogen embrittlement with high accuracy.

Means for Solving the Problem

To solve the above problem, according to claim 1, there is provided a steel fracture starting point estimation method for estimating a fracture starting point of steel, the method causing a computer to execute: a first step of calculating a hydrogen concentration distribution in steel-to-be-estimated when the steel fractures due to hydrogen embrittlement; a second step of calculating critical hydrogen content at which the steel-to-be-estimated fractures due to hydrogen embrittlement; and a third step of reading the hydrogen concentration distribution out of a storage unit, calculating, from the hydrogen concentration distribution, a location in the steel in which hydrogen concentration of the critical hydrogen content is distributed, and designating the location in the steel as the fracture starting point of the steel-to-be-estimated.

According to claim 2, in the steel fracture starting point estimation method according to claim 1, the first step includes calculating a hydrogen diffusion coefficient of the steel-to-be-estimated based on variation of hydrogen content in the steel with time on assumption that hydrogen diffuses in the steel, and calculating the hydrogen concentration distribution using a diffusion equation based on the hydrogen diffusion coefficient.

According to claim 3, in the steel fracture starting point estimation method according to claim 1 or 2, the first step includes calculating the hydrogen concentration distribution when the steel-to-be-estimated fractures with constant tensile stress being applied, and the second step includes charging the steel-to-be-estimated with hydrogen until saturation, calculating hydrogen content corresponding to the constant tensile stress using measurement data of tensile stress at fracture in a tensile test conducted repeatedly with an amount of charged hydrogen being varied, and designating the hydrogen content as the local critical hydrogen content.

According to claim 4, there is provided a steel fracture starting point estimation device that estimates a fracture starting point of steel, the steel fracture starting point estimation device comprising: a hydrogen concentration distribution calculation unit adapted to calculate a hydrogen concentration distribution in steel-to-be-estimated when the steel fractures due to hydrogen embrittlement; a local critical hydrogen content calculation unit adapted to calculate critical hydrogen content at which the steel-to-be-estimated fractures due to hydrogen embrittlement; and a fracture starting point estimation unit adapted to read the hydrogen concentration distribution out of a storage unit, calculate, from the hydrogen concentration distribution, a location in the steel in which hydrogen concentration of the critical hydrogen content is distributed, and designate the location in the steel as the fracture starting point of the steel-to-be-estimated.

According to claim 5, in the steel fracture starting point estimation device according to claim 4, the hydrogen concentration distribution calculation unit calculates a hydrogen diffusion coefficient of the steel-to-be-estimated based on variation of hydrogen content in the steel with time on assumption that hydrogen diffuses in the steel, and calculates the hydrogen concentration distribution using a diffusion equation based on the hydrogen diffusion coefficient.

According to claim 6, in the steel fracture starting point estimation device according to claim 4 or 5, the hydrogen concentration distribution calculation unit calculates the hydrogen concentration distribution when the steel-to-be-estimated fractures with constant tensile stress being applied; and the local critical hydrogen content calculation unit charges the steel-to-be-estimated with hydrogen until saturation, calculates hydrogen content corresponding to the constant tensile stress using measurement data of tensile stress at fracture in a tensile test conducted repeatedly with an amount of charged hydrogen being varied, and designates the hydrogen content as local critical hydrogen content.

According to claim 7, there is provided a steel fracture starting point estimation program that causes a computer to function as the steel fracture starting point estimation device according to any one of claims 4 to 6.

Effects of the Invention

The present invention makes it possible to estimate a fracture starting point of steel due to hydrogen embrittlement with high accuracy.

DESCRIPTION OF EMBODIMENTS

An embodiment of the present invention will be described below with reference to the drawings.

Configuration of Steel Fracture Starting Point Estimation Device

Figure 1:
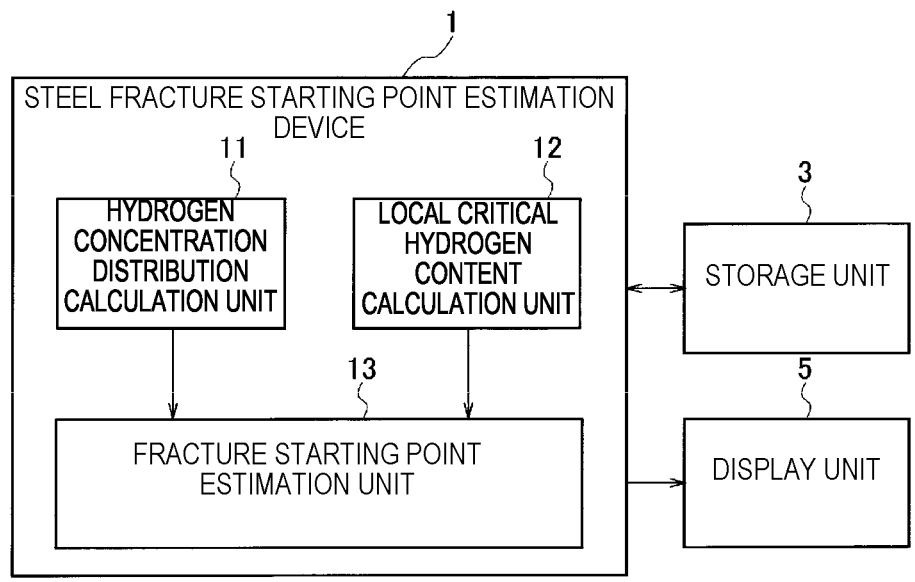
FIG. 1 is a diagram showing a configuration of a steel fracture starting point estimation device.

FIG. 1 is a diagram showing a configuration of a steel fracture starting point estimation device 1 according to the present embodiment. The steel fracture starting point estimation device 1 includes a hydrogen concentration distribution calculation unit 11, a local critical hydrogen content calculation unit 12, and a fracture starting point estimation unit 13. The steel fracture starting point estimation device 1 is connected to a storage unit 3 and display unit 5 in a communication-ready state via its communications interface.

The hydrogen concentration distribution calculation unit 11 has a function to calculate a hydrogen concentration distribution in high-strength steel to be estimated (hereinafter referred to as the steel-to-be-estimated or the steel) when the steel fractures due to hydrogen embrittlement and store the hydrogen concentration distribution in the storage unit 3. The hydrogen concentration distribution calculation unit 11 has a function to calculate a hydrogen diffusion coefficient of the steel-to-be-estimated based on variation of hydrogen content in the steel with time on assumption that hydrogen diffuses in the steel and calculate the hydrogen concentration distribution in the steel using a diffusion equation based on the calculated hydrogen diffusion coefficient. The hydrogen concentration distribution calculation unit 11 has a function to calculate the hydrogen concentration distribution in the steel-to-be-estimated when the steel fractures with constant tensile stress being applied.

The local critical hydrogen content calculation unit 12 has a function to calculate critical hydrogen content (local critical hydrogen content) at which the steel-to-be-estimated fractures due to hydrogen embrittlement. A tensile test is conducted by charging the steel-to-be-estimated with hydrogen until saturation. The local critical hydrogen content calculation unit 12 has a function to calculate hydrogen content corresponding to the constant tensile stress using measurement data of tensile stress at fracture in a tensile test conducted repeatedly with an amount of charged hydrogen being varied, and designate the hydrogen content as local critical hydrogen content.

The fracture starting point estimation unit 13 has a function to read data on the hydrogen concentration distribution out of the storage unit 3, calculate, from the hydrogen concentration distribution, a location in the steel in which hydrogen concentration of the critical hydrogen content (local critical hydrogen content) is distributed, and output the calculated location in the steel to the display unit 5 as a fracture starting point of the steel-to-be-estimated.

Operation of Steel Fracture Starting Point Estimation Device and the Like

Next, a steel fracture starting point estimation method performed by the steel fracture starting point estimation device 1 will be described. The steel fracture starting point estimation device 1 performs the following steps. To estimate a fracture starting point of high-strength steel, plural pieces of high-strength steel of the same shape and same material are prepared in advance.

Step 1;

In step 1, a hydrogen concentration distribution in steel is calculated when the steel fractures due to hydrogen embrittlement. Step 1 will be described concretely below.

Step 1-1;

First, the time until the steel fractures due to hydrogen embrittlement is measured. Step 1-1 will be described concretely below.

According to the present embodiment, a constant-load test is conducted on steel rods by applying constant tensile stress to the steel rods while charging hydrogen into the steel rods and the time until the steel fractures is measured. That is, by continuing to charge the steel rods with hydrogen while maintaining constant tensile stress, the fracture time of the steel as a function of increase in hydrogen content is measured.

As test pieces of steel, for example, smooth round bars 50 cm long and 7 mm in diameter are used. As a method for hydrogen charging, a cathodic charging method is used, where the cathodic charging method involves immersing steel in an aqueous electrolytic solution and applying a negative potential. As a value of the constant load (tensile stress), stress 0.7 times the tensile strength of the steel is used. As the aqueous electrolytic solution, 1 mol/L of an aqueous sodium bicarbonate solution is used, and as an applied voltage, 1 V vs. SSE is used.

A constant-load test was conducted by applying tensile stress 0.7 times the tensile strength of the steel while charging hydrogen into the steel rods. A result was that the fracture time of the steel was 1.5 hours from the start of the hydrogen charging. A measurer stores the measured fracture time of the steel in the storage unit 3.

Step 1-2;

Next, a hydrogen diffusion coefficient of the steel is calculated based on variation of hydrogen content in the steel with time on assumption that hydrogen diffuses in the steel, and the hydrogen concentration distribution in the steel upon elapse of the fracture time of the steel measured in step 1-1 is calculated using a diffusion equation based on the calculated hydrogen diffusion coefficient. Step 1-2 will be described concretely below.

First, to calculate the hydrogen diffusion coefficient, the variation of hydrogen content in the steel with time is measured. In the present embodiment, using such stress (e.g., 0.5 times the tensile strength of the steel) that no fracture due to hydrogen embrittlement occurs as the stress for the constant-load test, the steel is charged with hydrogen by the same method as above, and the variation of hydrogen content in the steel with time is measured. In measuring the hydrogen content, for example, thermal desorption spectroscopy (TDS) is used. Regarding TDS measurement conditions, for example, measurements are taken up to a temperature of 500° C. at a temperature increase rate of 10° C./min.

Figure 2:
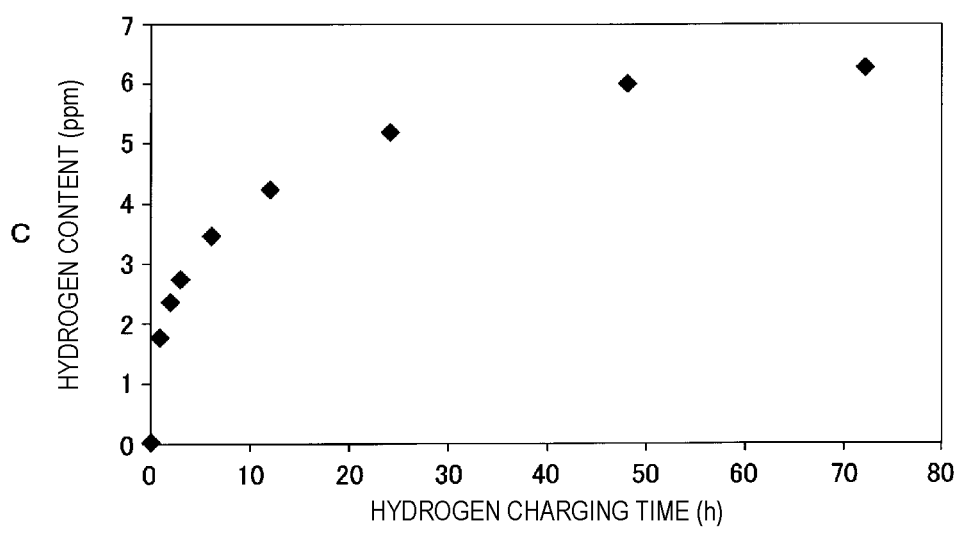
FIG. 2 is a diagram showing variation of hydrogen content in steel with time.

FIG. 2 is a diagram showing variation of hydrogen content in steel with time, where the variation of hydrogen content is obtained as measurement results. The abscissa represents hydrogen charging time t and the ordinate represents hydrogen content C in the steel at the hydrogen charging time t. It can be seen from FIG. 2 that the longer the hydrogen charging time t, the larger the hydrogen content C in the steel.

Since it is thought that the hydrogen in steel penetrates inside the steel by diffusion as described earlier, the hydrogen content C in the steel in an initial stage of diffusion can be approximated by Formula (1). The measurer stores Formula (1) in the storage unit 3.

Formula 1

$$\frac{C}{C_s} = \frac{4}{a}\left(\frac{Dt}{\pi}\right)^{\frac{1}{2}} \quad (1)$$

where C is the hydrogen content in steel, $C_s$ is saturated hydrogen content, a is the radius of steel, D is a hydrogen diffusion coefficient, and t is hydrogen charging time. Also, from FIG. 2, the saturated hydrogen content $C_s$ is as given by Formula (2).

Formula 2

$$C_s = 6.40(ppm) \quad (2)$$

The measurer stores the value of Formula (2), a radius a of the steel, and other values in the storage unit 3. The hydrogen concentration distribution calculation unit 11 reads Formula (1), Formula (2), the radius a of the steel, and other values out of the storage unit 3, and performs calculations by substituting the value of Formula (2), radius a of the steel, and other values into Formula (1). As a result, the hydrogen diffusion coefficient D is given by Formula (3).

Formula 3

$$D \cong 1.45 \times 10^{-1} (mm^2/h) \quad (3)$$

Next, using the calculated value of the hydrogen diffusion coefficient D as a diffusion coefficient and using an existing diffusion equation having the diffusion coefficient and time as variables, the hydrogen concentration distribution calculation unit 11 calculates the hydrogen concentration distribution in the steel at the time when fracture occurs in the steel (upon elapse of 1.5 hours found in step 1-1), for example, by a common numerical calculation method based on a difference method.

Figure 3:
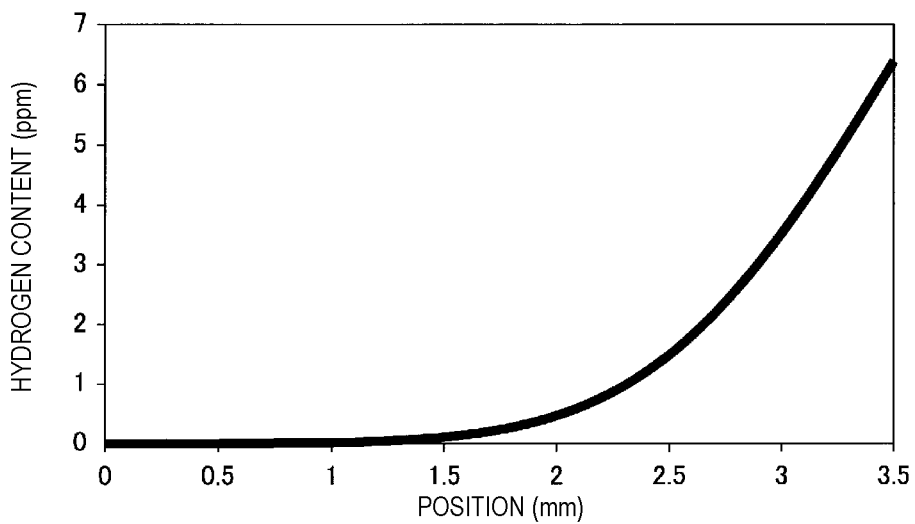
FIG. 3 is a diagram showing a hydrogen concentration distribution in steel when fracture occurs.

FIG. 3 is a diagram showing a hydrogen concentration distribution in steel when fracture occurs, where the hydrogen concentration distribution is obtained as calculation results. The abscissa represents the depth position along a diameter section of a round steel bar and the ordinate represents the hydrogen content at a sectional position of the diameter section. The left side of the abscissa (on the side of 0 mm) corresponds to the center side in the steel and the right side (on the side of 3.5 mm) corresponds to the surface side of the steel. It can be seen that a larger amount of hydrogen is distributed on the surface than inside the steel. The hydrogen concentration distribution calculation unit 11 stores data on the calculated hydrogen concentration distribution in the storage unit 3.

Step 2;

The hydrogen concentration distribution in steel when the steel fractures due to hydrogen embrittlement has been found in step 1. In step 2 and after-mentioned step 3, based on the hydrogen concentration distribution, along a diameter section in steel, the depth position of the hydrogen content that causes hydrogen embrittlement fracture is identified, and thereby a fracture starting point of the steel due to hydrogen embrittlement is estimated.

Thus, in step 2, a local hydrogen content (local critical hydrogen content) threshold at or above which hydrogen embrittlement fracture occurs is calculated. To measure the local critical hydrogen content, for example, a CSRT method (Non-Patent Literature 4) is used. With the CSRT method, to conduct a tensile test in such a short time that the hydrogen in steel will not undergo stress-induced diffusion, hydrogen content uniformly absorbed in the steel in advance can be assumed to be equal to the local critical hydrogen content.

Specifically, the steel is charged with hydrogen until the hydrogen content reaches saturation under no-load conditions, then a tensile test is conducted at a tension speed of 1 mm/min, and tensile stress is measured when the steel is fractured. The hydrogen content at the time when hydrogen reaches saturation is measured using TDS (thermal desorption spectroscopy) described above. The tensile test is conducted repeatedly with an applied potential for hydrogen charging being varied and the hydrogen content at the time when saturation is reached being thereby varied. The measurer stores measurement data of the tensile test in the storage unit 3.

Figure 4:
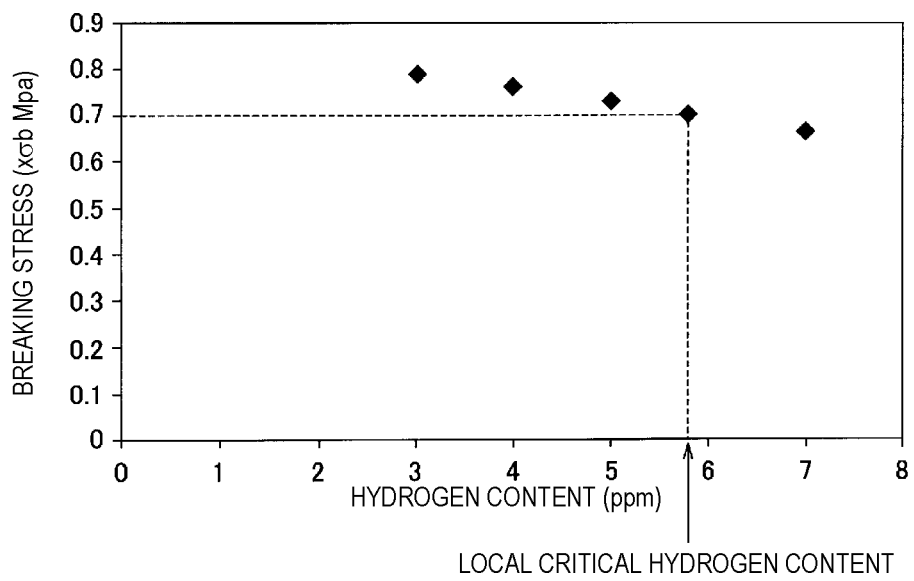
FIG. 4 is a diagram showing changes in fracture stress when tensile test is conducted by varying hydrogen content in steel.

FIG. 4 is a diagram showing changes in fracture stress when tensile test is conducted by varying hydrogen content in steel. The abscissa represents hydrogen content and the ordinate represents breaking stress (=tensile stress) at the time when the steel fractures. The larger the hydrogen content, the lower the stress that breaks the steel, and it can be seen that the smaller the hydrogen content, the higher the stress needed to break the steel.

Using the measurement results of tensile test shown in FIG. 4, the local critical hydrogen content calculation unit 12 calculates the hydrogen content with which fracture occurs at tensile stress (=the tensile stress used in the constant-load test of step 1-1) 0.7 times the tensile strength of the steel and designates the calculated hydrogen content as local critical hydrogen content under a stress condition in which the tensile stress is 0.7 times the tensile strength. The local critical hydrogen content calculation unit 12 stores the calculated local critical hydrogen content in the storage unit 3.

Step 3;

Based on consideration of the local critical hydrogen content, as described in Background Art, fracture of steel due to hydrogen embrittlement occurs when local hydrogen content in the steel reaches or exceeds the local critical hydrogen content. That is, in FIG. 3 that shows a hydrogen concentration distribution at the time when fracture occurs, it is thought a fracture starting point exists in an inner region of the steel in which local hydrogen content is equal to or higher than the local critical hydrogen content.

Figure 5:
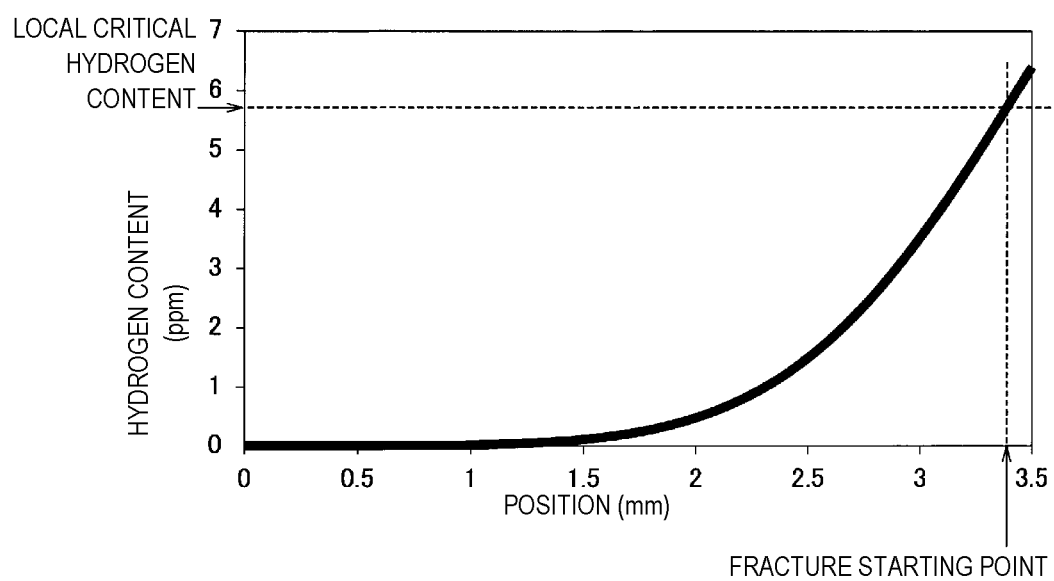
FIG. 5 is a diagram showing a method for estimating a fracture starting point.

Therefore, the fracture starting point estimation unit 13 reads the data on the calculated hydrogen concentration distribution as well as the local critical hydrogen content out of the storage unit 3, and calculates, from the hydrogen concentration distribution, a location in the steel in which hydrogen concentration of the local critical hydrogen content is distributed as shown in FIG. 5, and outputs the calculated location in the steel to the display unit 5 as a fracture starting point of the steel-to-be-estimated. In the case of FIG. 5, the fracture starting point estimation unit 13 estimates that the fracture starting point exists within 90 μm inward from the surface of the round steel bar test piece.

Thus, according to the present embodiment, since the steel fracture starting point estimation device 1 includes the hydrogen concentration distribution calculation unit 11 adapted to calculate a hydrogen concentration distribution in steel-to-be-estimated when the steel fractures due to hydrogen embrittlement; the local critical hydrogen content calculation unit 12 adapted to calculate critical hydrogen content at which the steel-to-be-estimated fractures due to hydrogen embrittlement; and the fracture starting point estimation unit 13 adapted to read the hydrogen concentration distribution out of the storage unit 3, calculate, from the hydrogen concentration distribution, a location in the steel in which hydrogen concentration of the critical hydrogen content is distributed, and designate the location in the steel as the fracture starting point of the steel-to-be-estimated, the fracture starting point of the steel due to hydrogen embrittlement can be estimated with high accuracy.

For example, the fracture starting point of hydrogen embrittlement can be estimated with high accuracy on the order of 10 μm, which has been difficult before. Once the fracture starting point can be estimated, the fracture time with hydrogen charging conditions (i.e., the value of C s) changed can be predicted and the fracture time can be easily known without many tests.

Finally, the steel fracture starting point estimation device 1 described in the present embodiment can be implemented by a computer and programs, where the programs can be recorded on a recording medium or provided via a communications network.

REFERENCE SIGNS LIST

1 Steel fracture starting point estimation device
11 Hydrogen concentration distribution calculation unit
12 Local critical hydrogen content calculation unit
13 Fracture starting point estimation unit
3 Storage unit
5 Display unit

The invention claimed is:

1. A steel fracture starting point estimation method for estimating a fracture starting point of steel, the method causing a computer to execute:

a first step of calculating a hydrogen concentration distribution in steel-to-be-estimated when the steel fractures due to hydrogen embrittlement;

a second step of calculating critical hydrogen content at which the steel-to-be-estimated fractures due to hydrogen embrittlement; and a third step of reading the hydrogen concentration distribution out of a storage unit, calculating, from the hydrogen concentration distribution, a location in the steel in which hydrogen concentration of the critical hydrogen content is distributed, and designating the location in the steel as the fracture starting point of the steel-to-be-estimated, wherein the first step includes calculating a hydrogen diffusion coefficient of the steel-to-be-estimated based on variation of hydrogen content in the steel with time on assumption that hydrogen diffuses in the steel, and calculating the hydrogen concentration distribution based on the following diffusion equation:

$$\frac{C}{C_s} = \frac{4}{a}\left(\frac{Dt}{\pi}\right)^{\frac{1}{2}} \quad (1)$$

where C is a hydrogen content in the steel-to-be-estimated, $C_s$ is a saturated hydrogen content, α is a radius of the steel-to-be-estimated, D is the hydrogen diffusion coefficient, and t is a hydrogen charging tie.

2. The steel fracture starting point estimation method according to claim 1, wherein:

the first step includes calculating the hydrogen concentration distribution when the steel-to-be-estimated fractures with constant tensile stress being applied, and the second step includes charging the steel-to-be-estimated with hydrogen until saturation, calculating hydrogen content corresponding to the constant tensile stress using measurement data of tensile stress at fracture in a tensile test conducted repeatedly with an amount of charged hydrogen being varied, and designating the hydrogen content as the local critical hydrogen content.

3. A non-transitory computer storage device having stored thereon computer executable instructions that, when executed by a processor, cause a computing device to perform the steel fracture starting point estimation method for estimating a fracture starting point of steel according to claim 2.

4. A non-transitory computer storage device having stored thereon computer executable instructions that, when executed by a processor, cause a computing device to perform the steel fracture starting point estimation method for estimating a fracture starting point of steel according to claim 1.

5. A steel fracture starting point estimation device that estimates a fracture starting point of steel, the steel fracture starting point estimation device comprising:

a hydrogen concentration distribution calculation unit adapted to calculate a hydrogen concentration distribution in steel-to-be-estimated when the steel fractures due to hydrogen embrittlement;

a local critical hydrogen content calculation unit adapted to calculate critical hydrogen content at which the steel-to-be-estimated fractures due to hydrogen embrittlement; and a fracture starting point estimation unit adapted to read the hydrogen concentration distribution out of a storage unit, calculate, from the hydrogen concentration distribution, a location in the steel in which hydrogen concentration of the critical hydrogen content is distributed, and designate the location in the steel as the fracture starting point of the steel-to-be-estimated;
wherein the hydrogen concentration distribution calculation unit calculates a hydrogen diffusion coefficient of the steel-to-be-estimated based on variation of hydrogen content in the steel with time on assumption that hydrogen diffuses in the steel, and calculates the hydrogen concentration distribution based on the following diffusion equation:

$$\frac{C}{C_s} = \frac{4}{a}\left(\frac{Dt}{\pi}\right)^{\frac{1}{2}} \quad (1)$$

where C is a hydrogen content in the steel-to-be-estimated, $C_s$ is a saturated hydrogen content, $\alpha$ is a radius of the steel-to-be-estimated, D is the hydrogen diffusion coefficient, and t is a hydrogen charging time.

6. The steel fracture starting point estimation device according to claim 5, wherein:
the hydrogen concentration distribution calculation unit calculates the hydrogen concentration distribution when the steel-to-be-estimated fractures with constant tensile stress being applied; and
the local critical hydrogen content calculation unit charges the steel-to-be-estimated with hydrogen until saturation, calculates hydrogen content corresponding to the constant tensile stress using measurement data of tensile stress at fracture in a tensile test conducted repeatedly with an amount of charged hydrogen being varied, and designates the hydrogen content as local critical hydrogen content.

7. A steel fracture starting point estimation program that causes a computer to function as the steel fracture starting point estimation device according to claim 6.

8. A steel fracture starting point estimation program that causes a computer to function as the steel fracture starting point estimation device according to claim 5.

* * * * *